US00PP27898P3

(12) United States Plant Patent
Brown

(10) Patent No.: US PP27,898 P3
(45) Date of Patent: Apr. 18, 2017

(54) ***WESTRINGIA FRUTICOSA* PLANT NAMED 'WES06'**

(50) Latin Name: *Westringia fruticosa*
Varietal Denomination: WES06

(71) Applicant: Graham Brown, Cobbity (AU)

(72) Inventor: Graham Brown, Cobbity (AU)

( * ) Notice: Subject to any disclaimer, the term of this patent is extended or adjusted under 35 U.S.C. 154(b) by 372 days.

(21) Appl. No.: 14/120,960

(22) Filed: Jul. 16, 2014

(65) Prior Publication Data

US 2016/0021806 P1 Jan. 21, 2016

(51) Int. Cl.
*A01H 5/02* (2006.01)

(52) U.S. Cl.
USPC ..... Plt./226

(58) Field of Classification Search
USPC ..... Plt./226
CPC ..... A01H 5/02
See application file for complete search history.

(56) References Cited

PUBLICATIONS https://ozbreed.wordpress.com/2014/02/13/low-horizon-westringia-is-a-dense-and-ultra-compact-ground-cover/; Feb. 13, 2014; 3 pages.*

* cited by examiner

*Primary Examiner* — Kent L Bell
(74) *Attorney, Agent, or Firm* — Samuel R. McCoy, Jr.

(57) ABSTRACT

'WES06' is a distinctive variety of *Westringia fruticosa* which is characterized by the combination of very short plant height, decumbent growth habit, and greyed-green leaves.

2 Drawing Sheets

Latin name of the genus and species: The Latin name of the genus and species of the novel variety disclosed herein is *Westringia fruticosa.*

Variety denomination: The inventive variety of *Westringia fruticosa* disclosed herein has been given the variety denomination 'WES06'.

BACKGROUND OF THE INVENTION

The present invention relates to a new and distinct perennial variety of *Westringia fruticosa*, which has been given the variety denomination of 'WES06'. Its market class is that of a shrub. 'WES06' is intended for use in general landscaping and as a decorative plant.

Parentage: The *Westringia fruticosa* variety 'WES06' is a seedling selection which resulted from a controlled pollination breeding program from 2005 to 2010 in Cobbitty, NSW Australia. 'WES06' is a progeny of an outcrossing breeding program which resulted from the cross pollination of female parent line *Westringia fruticosa* 'WES05' (unpatented) and a male parent line which is an unnamed sibling of *Westringia fruticosa* 'WES05' (unpatented). Controlled pollination of the parents occurred in 2005 and resulting seed from said cross was harvested in November 2007 and was sown in March of 2008 in accord with standard greenhouse propagation practices. In September of 2008, the resulting young plants were transplanted into 15 cm nursery containers and relocated to an outdoor trial area for field observations. Progeny were further observed for desired commercial characteristics, and in September 2010, one candidate was selected for its very low height, mounded habit, grey-green foliage and heavy flower habit. The cultivar was named 'WES06'.

Asexual Reproduction: 'WES06' was first propagated asexually by softwood cuttings at a commercial breeding facility in Cobbitty, New South Wales, Australia in 2010 and has since been asexually propagated by division through ten successive generations. The distinctive characteristics of the inventive 'WES06' variety are stable from generation to generation; plants of the variety produced by asexual reproduction maintain the distinguishing characteristics of the original plant.

SUMMARY OF THE INVENTION

'WES06' is a distinctive variety of *Westringia fruticosa* which is characterized by the combination of very short plant height, decumbent growth habit, and greyed-green leaves.

BOTANICAL DESCRIPTION OF THE PLANT

Figure 1:
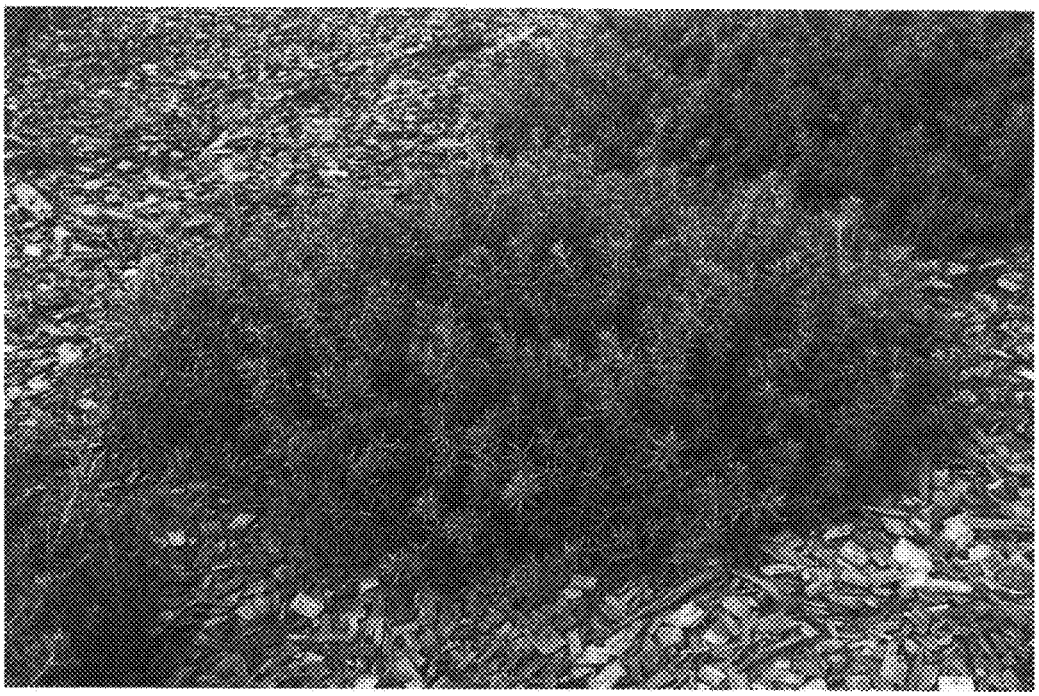
FIG. 1 shows an exemplary (approximate) 3-year old 'WES06' plant in the landscape.
Figure 2:
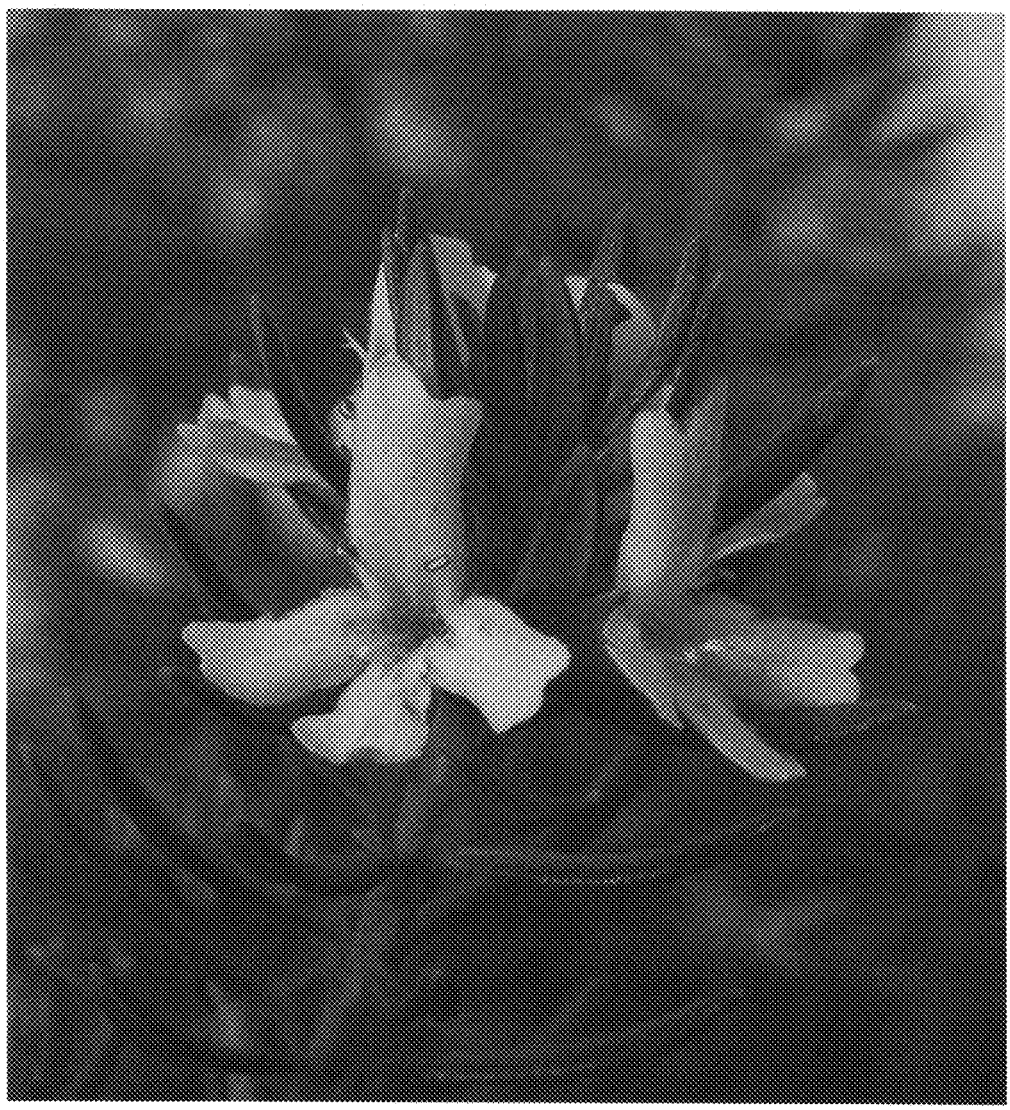
FIG. 2 shows an exemplary flower of 'WES06'.

The following is a detailed botanical description of a new and distinct variety of a *Westringia fruticosa* ornamental plant known as 'WES06'. Unless indicated otherwise, the descriptions disclosed herein are based upon observations made from an (approximate) 3-year old 'WES06' plant, established in a full-sun landscape in Richmond, New South Wales, Australia. Said plant was transplanted into the landscape from a fully-rooted 15 cm nursery pot, grown in soilless potting media, from rooted cuttings from May 2010 to November 2011. Once transplanted into the landscape, the observed plant was maintained with granular slow release fertilizer and regularly watered with overhead irrigation. No pest and disease measures were taken.

Those skilled in the art will appreciate that certain characteristics will vary with older or, conversely, younger plants. 'WES06' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 2001 edition. Note that generic color descriptions such as 'white' do not exist in the R.H.S. charts and the corresponding R.H.S. colors are quoted.

Technical Description of the Variety

Plant description:

*Plant habit.*—Shrub; very short height and dense, with a prostrate to decumbent growth habit.

*Height.*—200 mm.

*Width.*—1000 mm.

*Bloom period.*—Spring and sporadically at other times of year, depending on climate.

*Hardiness.*—USDA Zone 9 to 11.

*Propagation.*—Propagation is accomplished using semi-hard wood cuttings. Roots well without rooting compound or hormone.

*Time to develop roots.*—Approximately 3 to 4 weeks.

*Crop time.*—From approximately three to five months are needed to produce a well rooted 15 cm nursery pot, starting from a rooted cutting. Crop time varies with location and production practices.

*Pest and disease susceptibility or resistance.*—Neither resistance nor susceptibility to typical *Westringia fruticosa* pests and diseases has been observed.

Roots: The roots of 'WES06' are colored white and fleshy and thick, similar to other *Westringia fruticosa.*

Stem:

*Stem strength.*—Medium rigidity.

*Attitude.*—Prostrate to decumbent.

*Shape.*—Cylindrical yet angular.

*Stem color.*—Young stem is closest to green 137C.

*Stem dimensions.*—Mature stem, 6 nodes below the actively growing tip, are approximately 16 mm in length with a diameter of 1.7 mm.

*Stem surface.*—Corky and pruinose.

*Basal stem color.*—Mature stems closest to yellow green 199A.

*Internode length.*—12 mm on average.

Foliage:

*Type.*—Evergreen.

*Shape.*—Elliptical, narrow.

*Division.*—Simple.

*Apex.*—Acute.

*Base.*—Cuneate.

*Venation.*—Reticulate but not obvious.

*Vein color (adaxial surfaces).*—137A.

*Vein color (abaxial surfaces).*—192D.

*Margins.*—Entire.

*Arrangement.*—Whorled.

*Attachment.*—Petiolate.

*Texture.*—Leathery.

*Surfaces (adaxial surface).*—Finely pubescent to glabrous.

*Surfaces (abaxial surface).*—Heavily pubescent.

*Mature leaf dimensions.*—Average length, 18 mm; width is 3 mm.

*Leaf color (adaxial surface).*—137A.

*Leaf color (abaxial surface).*—192D.

*Petiole.*—Approximately 2 mm in length and the diameter is 0.75 to 1.0 mm; color is green, 137A, and heavily suffused with greyed-red, nearest to 182B.

*Stipules.*—Absent.

Inflorescence: Flowers are sessile.

Bud: Obovoid in shape and rounded at the apex. Approximately 5 mm long and 2.5 mm wide prior to dehiscence. Color is white 155A.

Flower:

*General.*—Flowers are sessile, simple and persist for approximately 5 days. Self cleaning. Non fragrant.

*Flowers.*—Small; Sympetalous, irregular with petals numbering five, width across the corolla measuring on average 12 mm; length of the perianth, from base of calyx to the furthest outstretched point of the corolla, measures 14 mm; color approximates to white N155D. Spots, or "eyes", present; color closest to violet 84B. Margins cilliate and slightly undulated; apex is emarginate; all surfaces are pubescent.

*Calyx.*—Synsepalous with five pointed sepal lobes; color is greyed-green 192B; apex of lobes are acute. The length of the calyx, including sepal lobes is 6 mm and the width of individual lobes at the widest point in 2.75 mm.

Reproductive organs:

*Stamens.*—4 and 2 staminodes.

*Attachment.*—Adnate.

*Filament color.*—Grey-brown 199A.

*Filament dimensions.*—About 4 mm in length and 0.75 mm in diameter.

*Anther dimensions.*—Bilobate; dorsifixed; approximately 1.0 to 1.25 mm long and 0.5 mm in diameter.

*Anther color.*—White 155D to yellow-white 158B and translucent.

*Pollen.*—Absent.

*Pistil.*—One.

*Pistil dimensions.*—About 7 mm in length and 0.5 mm in diameter.

*Pistil color.*—155D and slightly translucent.

*Ovary position.*—Inferior.

Fruit and seed: Observations not yet recorded.

Environmental tolerances:

*Cold and heat tolerance.*—The winter hardiness of 'WES06' is at least to USDA Zone 9a and evaluation of winter hardiness is ongoing. 'WES06' has heat tolerance typical of *Westringia fruticosa.*

*Drought tolerance.*—'WES06' has good drought tolerance typical of *Westringia fruticosa* once established.

*Pest resistance.*—No known insect pests. 'WES06' has disease tolerance typical of *Westringia fruticosa.*

*Cultural conditions.*—*Westringia* is commonly known to perform well in sandy soils, but also tolerates heavy, clay-type soils well. 'WES06' can also be grown in a relatively wide pH range and is also tolerant of above-normal salt concentration in the soil environment and is also tolerant of aerosol salt exposure; e.g. coastal exposure to salt laden winds.

Comparison of 'WES06' with the Parents

'WES06' is similar to the seed parent, *Westringia* 'WES05', in that both varieties have a low plant height and prostrate to decumbent growth habit. However, several distinguishing differences exist between the claimed plant And 'WES05'. 'WES06' is a short plant measuring approximately 20 cm in field grown trials, whereas 'WES05' plants of similar age are approximately 45 cm tall to the tallest branch. The flowers of 'WES06' are smaller than those of 'WES05'. The width across the perianth of 'WES05' is approximately 15 mm wide with a length, from base of calyx to the furthest outstretched petal, of approximately 21 mm, whereas the flower dimensions of 'WES06' are 12 mm across and 14 mm long.

'WES06' is similar to the unnamed *Westringia fruticosa* pollen parent in that both have shortened stem internodes, greyed-green leaves and small leaves. However, 'WES06' has a prostrate to decumbent growth habit, whereas the pollen parent has an upright to mounding growth habit. As such, the pollen parent grows to a much taller mature height when compared to 'WES06'.

Comparison of 'WES06' with the Most Similar Variety of *Westringia fruticosa*

'WES06' is most similar to the commercial variety *Westringia fruticosa* 'NFL25' (U.S. Plant Pat. No. 24,042), in that both varieties have a low plant height and prostrate to decumbent growth habit by comparison to the species, *Westringia fruticosa* common form. However, several distinguishing differences exist between the claimed plant and 'NFL25'. 'WES06' has a shorter plant height than 'NFL25'. 'WES06' is a short plant measuring approximately 20 cm in field grown trials whereas 'NFL25' plants of similar age are approximately 30 cm tall. The flowers of 'WES06' are smaller than those of 'NFL25'. The width across the perianth of 'NFL25' is both approximately 15 mm wide with a length, from base of calyx to the furthest outstretched petal, of approximately 21 mm whereas the flower dimensions of 'WES06' are 12 mm across and 14 mm long. The leaves of 'WES06' are smaller than those of 'NFL25'. The leaves of 'NFL25' measure 19.9 mm long and 4.1 mm wide, on average, whereas the leaves of 'WES06' have an average length and width of 18 mm and 3 mm, respectively.

That which is claimed is:

1. A new and distinct variety of *Westringia fruticosa* plant named 'WES06', substantially as described and illustrated herein.

* * * * *